(12) United States Patent
Barney et al.

(10) Patent No.: US 9,796,957 B2
(45) Date of Patent: Oct. 24, 2017

(54) GENETICALLY MODIFIED DIAZOTROPHS AND METHODS OF USING SAME

(71) Applicants: Brett Barney, Falcon Heights, MN (US); Carolann Marie Knutson, Apple Valley, MN (US); Mary Plunkett, St. Paul, MN (US)

(72) Inventors: Brett Barney, Falcon Heights, MN (US); Carolann Marie Knutson, Apple Valley, MN (US); Mary Plunkett, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/067,802

(22) Filed: Mar. 11, 2016

(65) Prior Publication Data

US 2016/0264929 A1    Sep. 15, 2016

Related U.S. Application Data

(60) Provisional application No. 62/131,532, filed on Mar. 11, 2015.

(51) Int. Cl.
| | |
|---|---|
| *C12N 1/20* | (2006.01) |
| *C12R 1/065* | (2006.01) |
| *C07K 14/21* | (2006.01) |
| *C12N 9/80* | (2006.01) |

(52) U.S. Cl.
CPC ............. *C12N 1/20* (2013.01); *C07K 14/21* (2013.01); *C12N 9/80* (2013.01); *C12R 1/065* (2013.01)

(58) Field of Classification Search
None
See application file for complete search history.

(56) References Cited

PUBLICATIONS

Meletzus et al., J. Bacteriol. 180(12):3260-3264, 1998.*
Masepohl et al., J. Bacteriol. 183(2):637-643, 2001.*
Masepohl et al. Mol. Gen. Genet., 212:27-37, 1988.*
Bali et al., Appl. Environ. Microbiol., 58(5):1711-1718, 1992.*
Bali, "Excretion of Ammonium by a nifL Mutant of *Azotobacter vinelandii* Fixing Nitrogen" 1992 *Appl. Environ. Microbiol.*, 58:1711-1719.
Barany, "Single-Stranded Hexameric Linkers: a System for in-Phase Insertion Mutagenesis and Protein Engineering" 1985 *Gene*, 37:111-123.
Barney, "Approaches to Improving the Potential of Azotobacter vinelandii as a Biofertilizer" Synthetic Biology Engineering Evolution Design Seed, Boston MA, Jun. 12, 2015, available online http://synbioconference.org/2015/proceeding/paper/approaches-improving-potential-azotobacter-vinelandii-biofertilizer [retrieved on Apr. 19, 2017].
Barney, "Substrate interaction at an iron-sulfur face of the FeMo-cofactor during nitrogenase catalysis" 2004 *J. Biol. Chem.*, 279:53621-53624.
Barney, "Trapping a hydrazine reduction intermediate on the nitrogenase active site" 2005 *Biochemistry*, 44:8030-8037.
Barney, "A substrate channel in the nitrogenase MoFe protein" 2009 *J. Biol. Inorg. Chem.*, 14:1015-1022.
Barney, "Gene Deletions Resulting in Increased Nitrogen Release by Azotobacter vinelandii: Application of a Novel Nitrogen Biosensor" Jul. 2015 *Appl Environ Microbiol.*, 81(13):4316-28. doi: 10.1128/AEM.00554-15. Epub Apr. 17, 2015.
Blanco, "Sequence and molecular analysis of the nifL gene of *Azotobacter vinelandii*" 1993 *Mol. Microbiol.*, 9:869-879.
Bouhenni, "Identification of genes involved in cytochrome c biogenesis in *Shewanella oneidensis*, using a modified mariner transposon" 2005 *Appl. Environ. Microbiol.*, 71:4935-4937.
Brechignac, "Pilot CELSS based on a maltose-excreting Chlorella: concept and overview on the technological developments" 1992. *Adv. Space Res.*, 12:33-36.
Brewin, "The basis of ammonium release in nifL mutants of Azotobacter vinelandii" Dec. 1999 *J Bacteriol.*, 181(23):7356-62.
Brutinel, "Anomalies of the anaerobic tricarboxylic acid cycle in *Shewanella oneidensis* revealed by Tn-seq" 2012 *Mol. Microbiol.*, 86:273-283.
Castorph, "Some properties of a *Klebsiella pneumoniae* ammonium transport negative mutant (Amt-)" 1984 *Arch. Microbiol.*, 139:245-247.
Chaurasia, "Improved Eco-Friendly Recombinant *Anabaena* sp. Strain PCC7120 with Enhanced Nitrogen Biofertilizer Potential" 2011 *Appl. Environ. Microbiol.*, 77:395-399.
Corbin "Liquid chromatographic-fluorescence determination of ammonia from nitrogenase reactions: a 2-min assay" 1984 *Appl. Environ. Microbiol.*, 47:1027-1030.
Dos Santos, "Molecular Biology and Genetic Engineering in Nitrogen Fixation" 2011 *Methods Mol. Biol.*, 766:81-92.
Fan, "Transcriptomic profiling of *Bacillus amyloliquefaciens* FZB42 in response to maize root exudates" 2012 *BMC Microbiol.*, 12.
Hill, "Environmental, economic, and energetic costs and benefits of biodiesel and ethanol biofuels" Jul. 2006 *Proc. Natl. Acad. Sci. U.S.A.*, 103:11206-11210.
Hu, "Microalgal triacylglycerols as feedstocks for biofuel production: perspectives and advances" 2008 *Plant J.*, 54:621-639.
Ikeda, "Community- and genome-based views of plant-associated bacteria: plant-bacterial interactions in soybean and rice" 2010 *Plant & Cell Physiol.*, 51:1398-1410.
International Fertilizer Industry Association, "Food Prices and Fertilizer Markets" 2011.

(Continued)

*Primary Examiner* — Nancy Treptow
(74) *Attorney, Agent, or Firm* — Mueting, Raasch & Gebhardt, PA

(57) ABSTRACT

This disclosure describes a genetically-modified diazotrophic microbe and methods that involve the genetically-modified diazotrophic microbe. Generally, the diazotrophic microbe is modified to excrete a nitrogen-containing compound in an amount greater than a comparable control diazotrophic microbe. The genetically-modified diazotrophic microbe can be co-cultured with a non-diazotroph and increase the growth of the non-diazotroph.

4 Claims, 8 Drawing Sheets

(56) References Cited

PUBLICATIONS

International Fertilizer Industry Association, "Fertilizer Facts: Nitrogen production: why energy feedstock trends are important," Sep. 2014.

International Fertilizer Industry Association, "Energy Efficiency and Co2 Emissions in Ammonia Production," Dec. 2009.

Johnson, "Controlled expression and functional analysis of iron-sulfur cluster biosynthetic components within Azotobacter vinelandii" Nov. 2006 *J. Bacteriol.* 188:7551-7561.

Kanda, "Determination of Ammonium in Seawater Based on the Indophenol Reaction with O-Phenylphenol (Opp)" 1995 *Water Res.*, 29:2746-2750.

Kumar, "Establishment of *Azotobacter* on plant roots: chemotactic response, development and analysis of root exudates of cotton (*Gossypium hirsutum* L.) and wheat (*Triticum aestivum* L.)" 2007 *J. Basic Microbiol.*, 47:436-439.

Leaungvutiviroj, "Development of a New Biofertilizer with a High Capacity for N-2 Fixation, Phosphate and Potassium Solubilization and Auxin Production" May 2010 *Biosci. Biotechnol. Biochem.*, 74:1098-1101.

Lenneman, "Fatty Alcohols for Wax Esters in *Marinobacter aquaeolei* VT8: Two Optional Routes in the Wax Biosynthesis Pathway" Nov. 2013 *Appl. Environ. Microbiol.*, 79:7055-7062.

Lenneman, "Potential application of algicidal bacteria for improved lipid recovery with specific algae" Apr. 2014 *FEMS Microbiol. Lett.* 354:102-110.

Lynch, "Substrate flow in the rhizosphere" 1990 *Plant and Soil*, 129:1-10.

Mather, The automated thiosemicarbazide-diacetyl monoxime method for plasma urea. May 1969 *Clin. Chem.*, 15:393-396.

Meletzus, "Characterization of the glnK-amtB Operon of *Azotobacter vinelandii*" Jun. 1998 *J. Bacteriol.*, 180:3260-3264.

Musa-Aziz, "Relative CO2/NH3 selectivities of AQP1, AQP4, AQP5, AmtB, and RhAG" Mar. 2009 *Proc. Natl. Acad. Sci. U.S.A.*, 106:5406-5411.

Musa-Aziz, "Concentration-Dependent Effects on Intracellular and Surface pH of Exposing Xenopus oocytes to Solutions Containing NH3/NH4+" Mar. 2009 *J. Membrane Biol.*, 228:15-31.

Ortiz-Marquez, "Genetic engineering of multispecies microbial cell factories as an alternative for bioenergy production" 2013 *Trends in Biotechnology*, 31:521-529.

Ortiz-Marquez, "Metabolic engineering of ammonium release for nitrogen-fixing multispecies microbial cell-factories" 2014 *Metab. Eng.*, 23:154-164.

Ortiz-Marquez, "Association with an Ammonium-Excreting Bacterium Allows Diazotrophic Culture of Oil-Rich Eukaryotic Microalgae" Jan. 2012 *Appl. Environ. Microbiol.*, 78:2345-2352.

Prentki, "In vitro insertional mutagenesis with a selectable DNA fragment" Sep. 1984 *Gene*, 29:303-313.

Sarma, "Crystal Structure of the L Protein of *Rhodobacter sphaeroides* Light-Independent Protochlorophyllide Reductase with MgADP Bound: A Homologue of the Nitrogenase Fe Protein" 2008 *Biochemistry*, 47:13004-13015.

Sashidhar, "Mineral phosphate solubilization by rhizosphere bacteria and scope for manipulation of the direct oxidation pathway involving glucose dehydrogenase" 2010 *J. Appl. Microbiol.*, 109:1-12.

Searchinger, "Use of US croplands for biofuels increases greenhouse gases through emissions from land-use change" 2008 *Science*, 319:1238-1240.

Setubal, "Genome Sequence of *Azotobacter vinelandii*, an Obligate Aerobe Specialized to Support Diverse Anaerobic Metabolic Processes" Jul. 2009 *J. Bacteriol.*, 191:4534-4545.

Sheehan, "A look back at the U.S. Department of Energy Aquatic Species Program: Biodiesel from Algae" National Renewable Energy Laboratory, Jul. 1998.

Singh, "Landmark research in legumes" 2007 *Genome*, 50:525-537.

Smil, "Enriching the earth: Fritz Haber, Carl Bosch, and the transformation of world food production" MIT Press, Cambridge, Mass. 2001.

Smith, "Structure. Nitrogenase reveals its inner secrets" 2002 *Science*, 297:1654-1655.

Spoehr, "The chemical composition of *Chlorella*; effect of environmental conditions" 1949 *Plant Physiol.*, 24:120-149.

Taylor, "A correction in the nucleotide sequence of the Tn9O3 kanamycin resistance determinant in pUC4K" Jan. 1988 *Nucleic Acids Res.*, 16:358.

Torrecilla, "*Azotobacter vinelandii* siderophore can provide nitrogen to support the culture of the green algae *Neochloris oleoabundans* and *Scenedesmus* sp. BA032" Feb. 2014 *FEMS Microbiol. Lett.*, 351:70-77.

Vo, "Mechanism for nitrogen isotope fractionation during ammonium assimilation by *Escherichia coli* K12" May 2013 *Proc. Natl. Acad. Sci. U.S.A.*, 110:8696-8701.

Winkler, "Amt/MEP/Rh proteins conduct ammonia" 2006 *Pflugers Arch.*, 451:701-707.

Yamamoto, "g-butyrolactone-dependent expression of the *Streptomyces* antibiotic regulatory protein gene srrY plays a central role in the regulatory cascade leading to lankacidin and lankamycin production in *Streptomyces rochei*" Feb. 2008 *J. Bacteriol.*, 190:1308-1316.

Yoshida, "Utilization of atmospheric ammonia by an extremely oligotrophic bacterium, *Rhodococcus erythropolis* N9T-4" 2014 *J. Biosci. Bioeng.*, 117:28-32.

Zhang, "Involvement of the ammonium transporter AmtB in nitrogenase regulation and ammonium excretion in *Pseudomonas stutzeri* A1501" 2012 *Res. Microbiol.*, 163:332-339.

* cited by examiner

US 9,796,957 B2

GENETICALLY MODIFIED DIAZOTROPHS AND METHODS OF USING SAME

CROSS-REFERENCE TO RELATED APPLICATION

This application claims priority to U.S. Provisional Patent Application Ser. No. 62/131,532, filed Mar. 11, 2015, which is incorporated herein by reference.

SEQUENCE LISTING

This application contains a Sequence Listing electronically submitted to the United States Patent and Trademark Office via EFS-Web as an ASCII text file entitled "11004640101_SequenceListing_ST25.txt" having a size of 8 KB and created on Mar. 9, 2016, as amended by the Sequence Listing electronically submitted to the United States Patent and Trademark Office via EFS-Web as an ASCII text file entitled "110-04640101-ver2_ST25.txt" having a size of 9 KB and created on Oct. 7, 2016. Due to the electronic filing of the Sequence Listing, the electronically submitted Sequence Listing serves as both the paper copy required by 37 CFR §1.821(c) and the CRF required by §1.821(e). The information contained in the Sequence Listing is incorporated by reference herein.

SUMMARY

This disclosure describes, in one aspect, a diazotrophic microbe genetically modified to excrete a nitrogen-containing compound in an amount greater than a comparable control diazotrophic microbe.

In some embodiments, the diazotrophic microbe can excrete nitrogen-containing compound in an amount effective to support the growth of a non-diazotroph in co-culture.

In some embodiments, the genetic modification includes a deletion or disruption of at least a portion of ureABC.

In some embodiments, the genetic modification includes a deletion or disruption of at least a portion of amtB.

In some embodiments, the genetic modification includes a deletion or disruption of at least a portion of nifA2.

In some embodiments, the nitrogen-containing compound includes urea or ammonium.

In some embodiments, the diazotrophic microbe is derived from *Azotobacter vinelandii*.

In another aspect, this disclosure describes a method of increasing growth of a non-diazotroph. Generally, the method includes co-culturing the non-diazotroph a genetically-modified diazotrophic microbe, the genetically-modified diazotrophic microbe provided in an amount effective to increase the growth of the non-diazotroph compared to growth of the non-diazotroph in the absence of the diazotrophic microbe.

In some embodiments, increasing the growth of the non-diazotroph includes increasing the growth rate of the non-diazotroph.

In some embodiments, increasing the growth of the non-diazotroph includes increasing the cell density of the non-diazotroph.

In some embodiments, increasing the growth of the non-diazotroph includes increasing the crop yield of the non-diazotroph.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
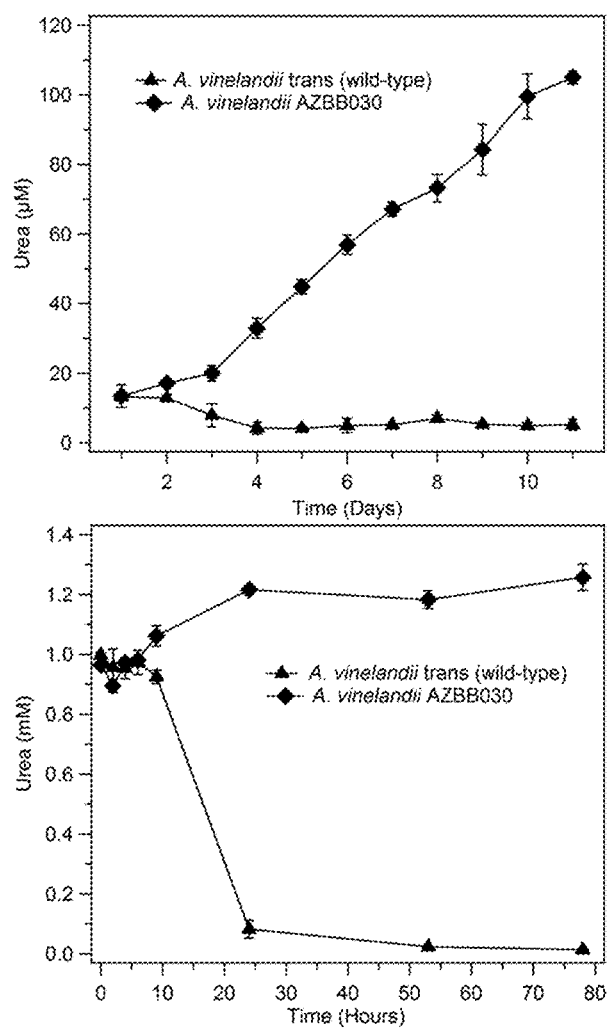
FIG. 1. Urea analysis of key *A. vinelandii* strains. Shown above are the results of urea analysis of the *A. vinelandii* wild-type strain and ΔureABC::strep$^R$ strain AZBB030. The top panel shows that urea levels in the AZBB030 increase over time versus the wild-type strain, reaching levels in excess of 100 µM. The bottom panel shows a similar experiment where both strains were provided approximately 1.2 mM of urea at the time of inoculation, indicating that strain AZBB030 does not metabolize urea to an appreciable amount, while the wild-type strain depletes the urea from the culture during the first 24 hours of growth. All results and statistics are calculated based on triplicate samples.

This disclosure describes several tools involving genetically-modified diazotrophic microbes to enhance nitrogen production and, therefore, support the growth of other organisms in co-culture. In one aspect, this disclosure describes a genetically-modified strain of a nitrogen-fixing microbe in which urea is a terminal product, resulting in release of urea to the extracellular space during growth. In another aspect, this disclosure describes a nitrogen biosensor strain that allows the screening of several hundred colonies on solid agar medium for extracellular nitrogen production. In yet another aspect, this disclosure describes methods of using the biosensor strain to screen several thousand colonies using transposon mutagenesis. The method allows one, for example, to identify a gene that, when disrupted, results in increased extracellular nitrogen production that is suitable for supporting the growth of both the biosensor strain and also alternative species such as algae when grown in co-culture.

Fertilizer inputs from industrial processes such as the Haber-Bosch process come at the expense of fossil fuels. *Azotobacter vinelandii* is a widely studied model diazotrophic (i.e., nitrogen fixing) bacterium, and also an obligate aerobe, differentiating it from many other diazotrophs that require environments low in oxygen for the function of the nitrogenase. Nutrient requirements are directly linked to biomass production, and any potential increased improvement in the scale of biomass yield will necessitate a proportional increase in the demand for essential nutrients. For all photosynthetic systems—e.g., photoautotrophs such as land plants, algae and cyanobacteria—with requisite light energy and water, nitrogen is a limiting and expensive nutrient input for aquaculture and agricultural production alike. Current nitrogen fertilizer production involves burning of fossil fuels to generate ammonia from molecular nitrogen ($N_2$ gas) through the Haber-Bosch process, which accounts for 3-5% of world natural gas consumption, or about 1-2% of the total worldwide energy expenditures. In developed countries, industrial nitrogen production is accompanied by a huge economic and energetic cost overall, while this key nutrient limits agricultural productivity in developing countries, where energy and infrastructure costs impede the use of the Haber-Bosch process to produce ammonia on a large scale from atmospheric nitrogen.

The development of improved biofertilizers represents a unique opportunity to lower the potential economic costs and environmental impacts of current fossil-fuel-dependent industrial methods for producing ammonia-derived fertilizers. *Azotobacter vinelandii* has been investigated as a possible tool for providing nitrogen to next generation biomass crops for many years, with varying degrees of success. While many nitrogen-fixing bacteria produce nitrogen in environments requiring very low oxygen, A. vinelandii has evolved the ability to fix nitrogen as a free living aerobe, despite nitrogenase being inherently sensitive to oxygen. This makes A. vinelandii an exemplary model organism for co-culture with a broader range of plants, as growth in micro-aerobic or anaerobic environments is not required. The ultimate long-term goal from these efforts would be to develop potential alternatives to the energy intensive Haber-Bosch process.

Biofertilizers provide a range of potential benefits versus current industrial nitrogen production routes. In situ biofertilizer production would displace and circumvent transportation costs and associated environmental impacts related to producing and distributing Haber-Bosch-derived industrial fertilizers. Biological assimilation of nutrients and/or timed-release of nitrogen compounds can mitigate issues associated with, for example, agricultural residue runoff from excessive application of industrial fertilizers, leading to eutrophication of nearby water supplies and streams. Both higher land plants and microalgae are known to produce extracellular carbon as a potential source of fixed carbon to support beneficial heterotrophs that make up part of the rhizosphere.

Current biofuel feedstock crops such as corn for ethanol require substantial amounts of nitrogen inputs. Potential future production of biomass using next generation feedstocks such as algae promise significant improvements in overall yield that could be orders of magnitude higher than current conventional land plant crops. Since current nitrogen requirements for the growth of biofuel crops are derived from energy intensive industrial processes such as Haber-Bosch, the energy use efficiency of current biofuel crops has been questioned. A significant amount of the energy acquired from, for example, corn ethanol, soybean biodiesel, and/or next generation biofuel crops (e.g., algae) may need to be diverted back to these industrial processes to supply the energy required for additional industrial nitrogen fixation. Improvements in final biomass yield can involve concomitant increases in macronutrient inputs such as nitrogen. Thus, the impacts and requirements of current methods to provide nitrogen for current and future crops will only increase in importance.

The approach described herein can circumvent the energy cost and the associated greenhouse gas emissions tied to producing and distributing nitrogen fertilizers by using a diazotrophic bacterium as a biofertilizer to provide a renewable source of nitrogen to meet the growth requirements of the associated photosynthetic species. While model symbiotic systems between specific plants and nitrogen-fixing bacteria are well established, these are limited to a small number of commodity crops. The approach described herein is directed towards expanding similar symbiotic relationships to a broader range of crops or next-generation biomass sources.

While described herein in the context of an exemplary embodiment in which the nitrogen-fixing microbe is Azotobacter vinelandii, the genetically-modified microbes and methods described herein can involve the use of other nitrogen-fixing species. For example, genes that correspond to Azotobacter vinelandii genes amtB and ureABC are natively present in, for example, other Azotobacter spp., Azoarcus spp., and Pseudomonas spp. Creating strains in alternative nitrogen-fixing microbes by making genetic modifications analogous to those described herein in the context of Azotobacter vinelandii is expected to produce genetically-modified strains that are phenotypically similar in relevant part to the strains expressly exemplified herein.

Urea as a Terminal Nitrogen Compound

Initially, Azotobacter vinelandii metabolism was modified to convert a common nitrogen metabolite into a terminal nitrogen product. Several target molecules were considered and urea was selected based on an analysis of A. vinelandii metabolic pathways and known enzymes. A. vinelandii contains coding regions for a known urease enzyme system (ureABC). Substitution of the ureABC operon with a streptomycin antibiotic marker resulted in a strain (AZBB030) that was unable to metabolize extraneously provided urea, even after several days, while the wild-type A. vinelandii strain is able to clear as much as 2-3 mM of urea within a day from the start of exponential growth (FIG. 1, bottom). This demonstrated that urea could become a terminal product in AZBB030.

In addition to removing the urease enzyme system so that urea could not be recycled in the cell, a foreign arginase coding region was added, since initial genomic analysis indicates that A. vinelandii does not contain a known arginase coding region. However, during control experiments to test several potential arginase coding regions from other species, the ΔureABC::strep$^R$ strain AZBB030 accumulated urea naturally (FIG. 1, top), either through the action of a yet to be characterized arginase enzyme system, or through alternative metabolic pathways present in A. vinelandii that yield urea as a by-product. This accumulation of urea in the µM range (approximately 100 µM after about 10 days of culture under the conditions used here), resulted in only slight improvements supporting the growth of non-diazotrophic strains in co-culture, but indicated a potential to increase urea levels. Thus, further efforts to incorporate a foreign arginase were suspended, though the possibility of identifying a potential novel arginase or urea cycle from A. vinelandii remains a possible alternative approach.

Construction of a Nitrogen Biosensor Strain

Figure 2:
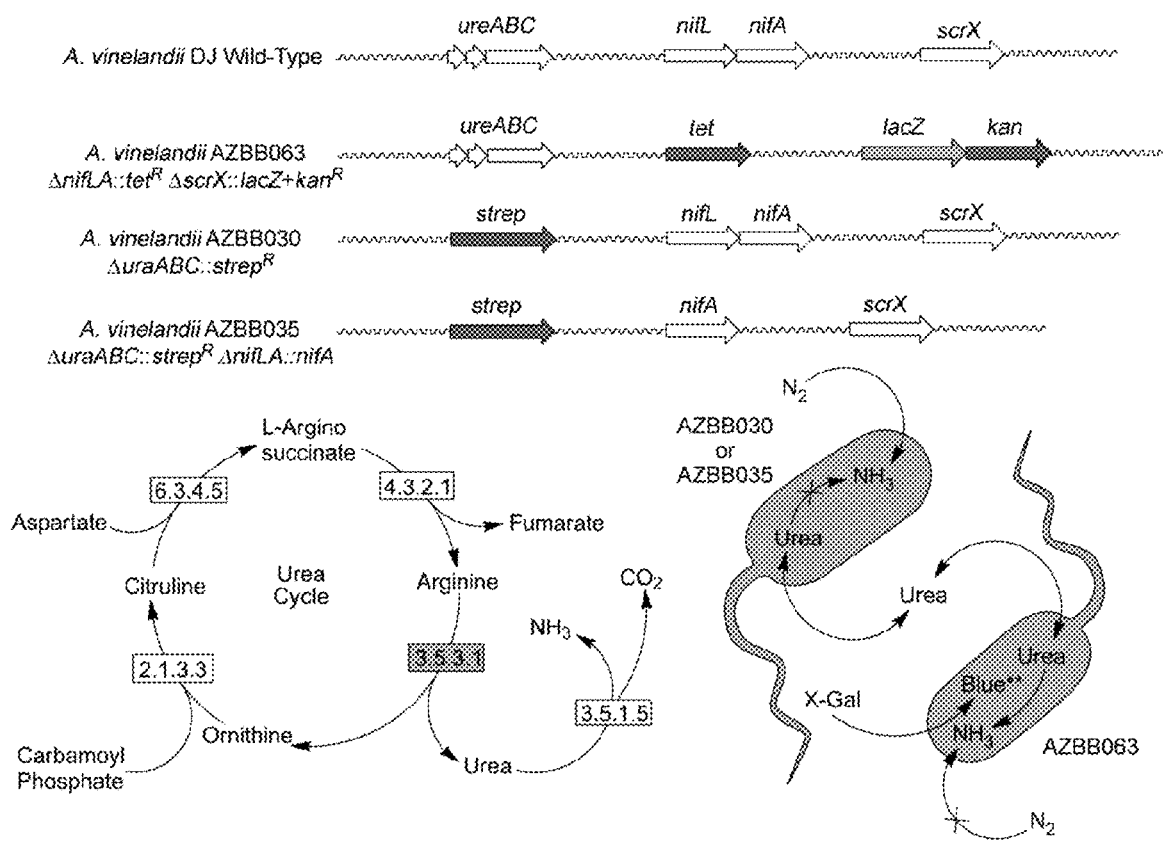
FIG. 2. Descriptions of various strains constructed for this work. Shown above are simple representations of modifications made to various regions of the *A. vinelandii* genome to construct the nitrogen biosensor strain AZBB063 which results in minimal growth in the absence of extraneously provided nitrogen and yields a blue phenotype when grown in the presence of X-Gal. Additional constructs AZBB030 and AZBB035 contain ΔureABC::strep$^R$, resulting in the accumulation of minor amounts of urea (FIG. 1). AZBB035 also contains a deregulated nitrogenase by first removing the nifLA genes, then replacing them with nifA behind the nifL promoter, resulting in a rescued nitrogen-fixing phenotype. The bottom left shows the urea cycle and urease enzyme (3.5.1.5) as it has been annotated in *A. vinelandii*. A known gene for arginase (3.5.3.1) has not been identified in *A. vinelandii*. The bottom right illustration indicates how urea as a terminal product could potentially support the growth of the nitrogen biosensor AZBB063 if quantities of urea increased to a level sufficient to meet the nitrogen requirements of this strain. Additional metabolites produced by the AZBB030 and AZBB035 strains following transposon mutagenesis experiments could also substitute for the urea in this representation, as was found in these studies.

Second, a strain that could serve as an indicator of extracellular nitrogen products was identified for application in screens. Initially, several strains of alternative bacteria were considered as possible candidates for this role, based on physical characteristics such as, for example, color, which would make the indicator bacteria easy to distinguish or differentiate on plates. However, this involves incorporating antibiotic selection markers to be grown together with transposon-treated A. vinelandii, and did not guarantee that these strains would be able to utilize all of the potential extracellular forms of nitrogen produced by A. vinelandii. Alternatively, a strain of A. vinelandii that could fulfill this biosensor purpose was constructed. First, lacZ from Escherichia coli MG1655 was incorporated into A. vinelandii directly downstream of the scrX promoter as described previously (Dos Santos P C, 2011, Methods Mol. Biol. 766:81-92; Johnson et al., 2006, J. Bacteriol. 188:7551-7561), resulting in a blue colored phenotype when grown in the presence of X-Gal. Next, the nitrogenase regulatory genes nifLA were replaced with a tetracycline antibiotic marker. These genes are involved in regulating expression of nitrogenase when molybdenum is available. This modification resulted in a strain that grew extremely slowly in the absence of extraneously provided nitrogen sources such as ammonium or urea (nif$^-$), but grew well when these nitrogen sources were provided as a component of the medium. Together, this new strain (AZBB063) met all the desired requirements of the nitrogen biosensor described herein: requiring extraneous nitrogen for growth, producing an easily-detectable signal, and having a strong potential to metabolize any nitrogen-containing metabolites that might be excreted by a modified or wild-type diazotrophic microbe. A diagram of the alterations made to the AZBB063 nitrogen biosensor strain versus wild-type *A. vinelandii* is shown in FIG. 2.

Initial Attempts to Construct a Deregulated Nitrogenase Strain

In addition to the ΔureABC::strep$^R$ strain (AZBB030) that accumulates low levels of urea, a deregulated nitrogenase strain was constructed. The nifLA substituted strain (AZBB030) containing a streptomycin selection marker was transformed with a plasmid that would incorporate nifA behind the promoter for nifL, resulting in a phenotype that is deregulated for nitrogenase production. Isolating the strain containing nifA in place of nifLA (AZBB035) rescued the nitrogen-fixing phenotype (nif$^+$) capable of growth on standard B plates, but did not result in copious quantities of ammonium being released into the supernatant. When either AZBB030 or AZBB035 were grown on a plate in the presence of the nitrogen biosensor strain AZBB063, extracellular nitrogen produced by either strain—in the form of either urea or ammonium—was not sufficient to support significant growth of AZBB063, as was found in experiments described below for other strains.

Transposon Mutagenesis Experiments to Increase Nitrogen Output

Figure 3:
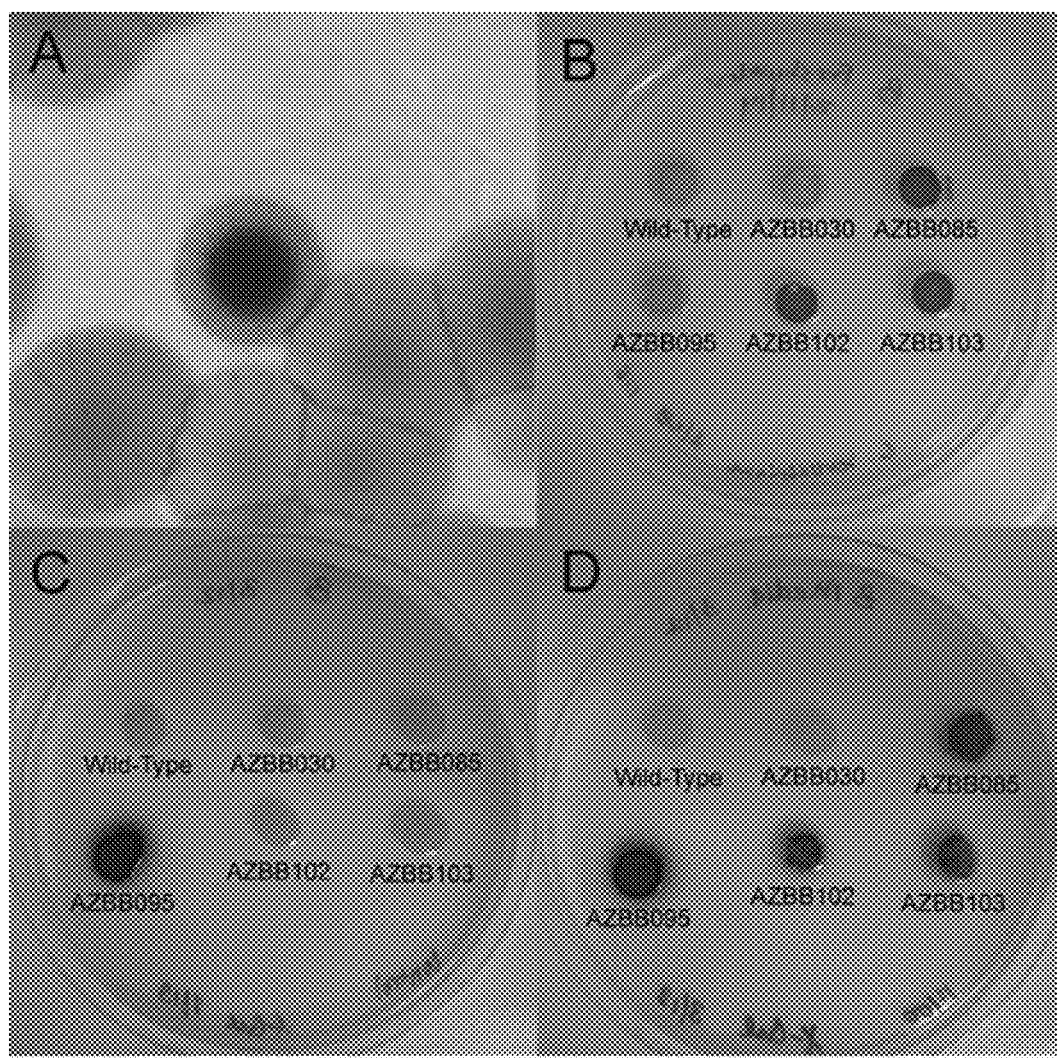
FIG. 3. Phenotypes of various *A. vinelandii* strains constructed or obtained in these studies. Shown in panel A is an example of the blue phenotype found for a specific colony using the screening technique with the nitrogen biosensor strain AZBB063 during the transposon mutagenesis experiment. Panel B shows various strains of *A. vinelandii* constructed for this study and grown as spots on a derivation of B medium with *C. sorokiniana* to determine if the strain could provide sufficient nitrogen to support the growth of the green algae. Panel C shows an example of a screen for false-positive strains that had unintentionally obtained the lacZ gene from the AZBB063 strain, resulting in a false-positive phenotype when screened together with AZBB063. In this experiment, pure strains were grown alone on B media supplemented with X-Gal. Panel D shows the various strains spotted onto a B plate together with a small amount of AZBB063 and X-Gal. These results indicate that strains AZBB085, AZBB102 and AZBB103 are all able to support the growth of a second strain (either AZBB063 or *C. sorokiniana*) that is unable to obtain nitrogen through the action of a functioning internal nitrogenase.

With the target strains AZBB030 and AZBB035 and the nitrogen biosensor AZBB063 strain in hand, transposon mutagenesis was used to introduce random gene disruptions and look for a phenotype that results in the production of extracellular nitrogen products. Using the techniques described in the EXAMPLES section, below, conjugated cells of AZBB030 or AZBB035 were spread over a plate containing a lawn of AZBB063 along with X-Gal and kanamycin, then grown for several days until colonies developed, indicating insertion of the transposon within the genome. The initial plate used to select colonies is devoid of added nitrogen compounds so that any insertions resulting in an undesirable disruption to nitrogen fixation or essential genes would be lost. After several additional days, numerous colonies turned blue indicating potential extracellular nitrogen production (FIG. 3A). Approximately 15 colonies were isolated, from approximately 3000 screened, by careful transfer and the phenotypes were confirmed and tested more thoroughly. These strains were grown up and genomic DNA obtained, then PCR was performed to amplify the transposon and genomic region where the transposon was incorporated.

Approximately half of the colonies isolated contained the blue phenotype when grown in the presence of X-Gal, even in the absence of the nitrogen biosensor strain AZBB063 (FIG. 3C). Sequencing revealed that lacZ and the downstream kanamycin cassette from the AZBB063 strain (FIG. 2) had been transferred to either the AZBB030 or AZBB035. This false positive result may be due to the survival of a small amount of the *E. coli* WM3064 conjugation strain that introduced lacZ from the indicator strain AZBB063 to the nitrogen-fixing target strains following plating on solid medium. The false positive was easily differentiated from strains with a true positive result, which only revealed the blue phenotype when grown together with the AZBB063 strain. An alternative construction of the indicator strain separating the kanamycin antibiotic selection marker from the lacZ gene should minimize the potential of these false positive strains in future experiments. While this false positive result is an unfortunate occurrence, less than ten total colonies out of several thousand screened exhibited the false positive result.

Strains yielding the correct blue phenotype when co-cultured with AZBB063 were identified and tested by spotting a small amount of each strain together with the green algae *Chlorella sorokiniana* onto a B plate (without nitrogen) to determine if the strain could provide sufficient extracellular nitrogen to support the growth of this algal strain. FIG. 3B shows an example of one such strain (AZBB085) that supported the growth of *C. sorokiniana* while wild-type and the initial targets AZBB030 or AZBB035 did not. Strain AZBB095, a false positive strain, was also unable to support the growth of *C. sorokiniana* (FIGS. 3B and 3C). Testing the potential to support an algal strain is a nice secondary screen, though whether a specific strain of algae can utilize the various extracellular nitrogen compounds produced is likely strain dependent, and is still considered inferior to the nitrogen biosensor strain AZBB063.

Figure 4:
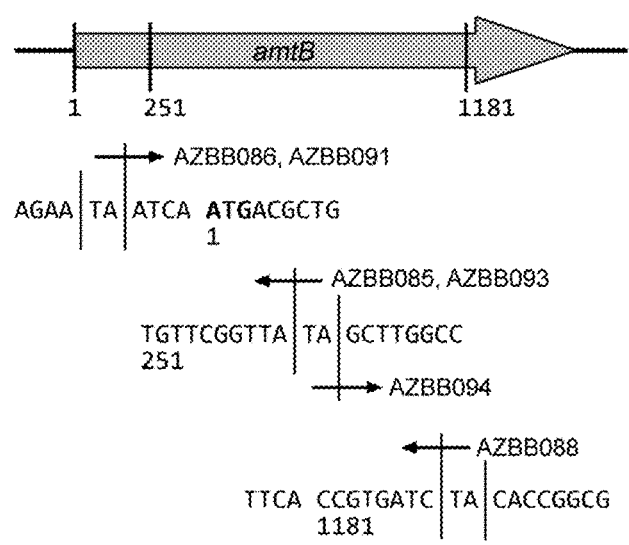
FIG. 4. Insertions into amtB resulting in nitrogen production phenotypes. Shown above is a drawing of the amtB gene region of *A. vinelandii*. The three different regions where insertions were found in this study during the nitrogen production screen are marked on the diagram, and the sequence of each region (SEQ ID NO:38, SEQ ID NO:39, and SEQ ID NO:40) is shown below. Specific TA base regions where insertions were made are marked with dividers on either side, and arrows are included depicting the region that was sequenced immediately outside of the transposon inverted repeat when sequenced with a primer that complemented a segment within to the kanamycin selection marker from within the transposon. Specific strain numbers from Table 1 are labeled beside each arrow.

Strain AZBB085 and five additional strains showed the correct blue phenotype with AZBB063. Each of these strains had the kanamycin cassette transposon inserted into amtB, and this occurred in both AZBB030-derived and AZBB035-derived colonies. While it was possible that some of the colonies could be replicates of the same transposon insertion event, only one of the six cases isolated here contained the same insertion and orientation for the same conjugation experiment (into either AZBB030 or AZBB035). In all other cases, the insert was either in a different location, or inserted in a different direction (FIG. 4). This result indicated a strong potential for developing this phenotype through a targeted substitution of the entire amtB gene.

A strategy to substitute amtB using a standard double homologous recombination genetic technique reduced the possibility that the phenotype might be the result of multiple transposon insertions. The amtB gene may be involved in transporting ammonia and/or ammonium, though a specific role in *A. vinelandii* is still unclear. Three explanations for the nitrogen secreting phenotype following amtB disruption were investigated. First, deleting amtB might result in increased extracellular ammonium if loss of this gene hindered the ability of the strain to recover ammonia or ammonium that leaks from the cell by natural processes. Second, amtB could be involved in urea uptake in addition to ammonia transport. Finally, amtB might be involved in transporting an alternative nitrogen compound, which requires the amtB still present in the AZBB063 indicator strain to transport this compound. Any of these explanations would still support a successful application of this approach to yield a strain of *A. vinelandii* with increased biofertilizer potential. To rule out the second option, amtB gene deletion/replacements were done to both strains containing ΔureABC::strep$^R$ and also to wild-type AV trans.

Construction of an amtB Deletion/Replacement *A. vinelandii* Strain

Using the same approach that was taken to generate strains AZBB030, AZBB035, and AZBB063, strains AZBB102 and AZBB103 were constructed. AZBB102 contains only ΔamtB::kan$^R$, while AZBB103 contains ΔamtB::kan$^R$ along with ΔureABC::strep$^R$. Both strains resulted in the blue phenotype when grown together with AZBB063 and also supported the growth of *C. sorokiniana* when a nitrogen source was not supplemented in the medium (FIGS. 3B and 3D). This indicates that urea is not the likely agent responsible for the observed phenotype, which was further confirmed by determining that urea production had not increased versus AZBB030 and AZBB035 levels in these strains (results similar to FIG. 1, not shown).

Analysis of Ammonium Production by Strains AZBB102 and AZBB103

The question of whether amtB transport of ammonia and/or ammonium was responsible for supporting the growth of either the algae or strain AZBB063 was investigated. Cells were grown for as long as a week, while supernatant was removed and ammonium was quantified using several different techniques as previously described (Ortiz-Marquez et al., 2012, *Appl. Environ. Microbiol.* 78:2345-2352; Barney et al., 2009, *J. Biol. Inorg. Chem.* 14:1015-1022; Barney et al., 2004, *J. Biol. Chem.* 279: 53621-53624; Kanda J, 1995, *Water Res.* 29:2746-2750). Modifications to the nifLA operon can result in the production of copious amounts of ammonium. The analysis of the supernatant from strain AZBB102 versus *A. vinelandii* trans (wild-type) found elevated levels of ammonium in the media, but levels were in the low µM range (FIG. 5), which is differentiated from previous reports with nifLA modifications (7-9).

Figure 5:
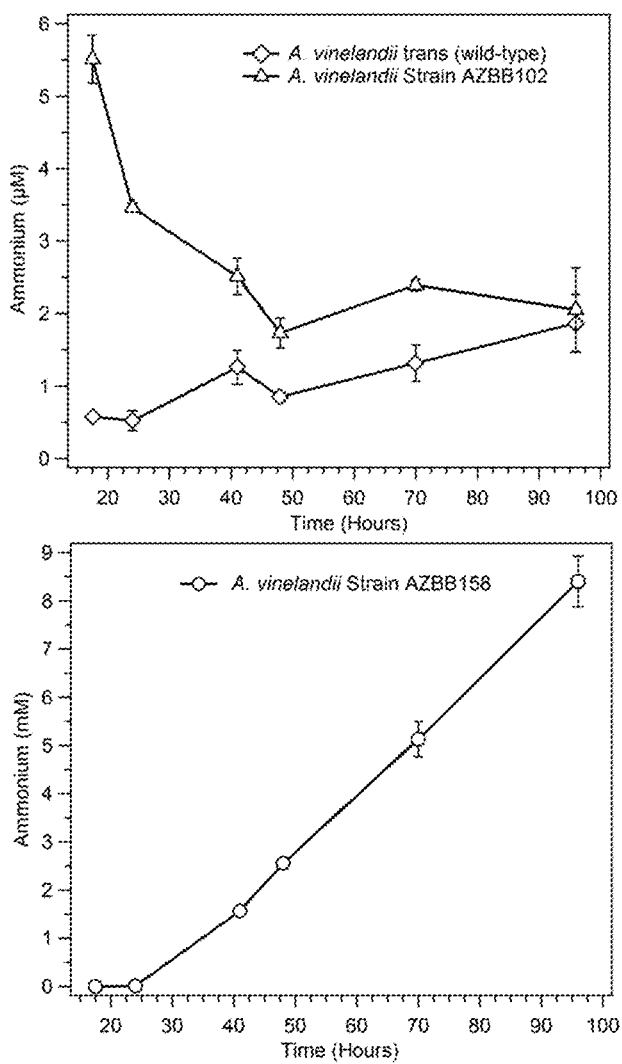
FIG. 5. Ammonium levels accumulating in *A. vinelandii* strain supernatants. Shown are the results from an analysis of *A. vinelandii* strain supernatants for the wild-type and strain AZBB102 that contains $\Delta amtB::kan^R$ (upper graph). Levels of ammonium are consistently higher for strain AZBB102, though the levels found decrease over time, and were not found to increase above 10 µM during the entire experiment. The highest levels of ammonium were found early during the growth, while the strain was still in the exponential stage of growth. Levels of ammonium found in the nifLA disruption resulted in a phenotype that accumulated significant amounts of ammonium, though these levels did not begin to increase until the cells had reached a stationary phase of growth, after 24 hours. Averages and standard deviations shown are the results of triplicates. All cultures were grown at 22° C. while shaking at 160 rpm.

There is a strong debate currently about the role that amtB plays in the transport of ammonia or ammonium, including reports of increasing extracellular ammonium when amtB is deleted while also demonstrating that cells can obtain ammonium from the extracellular space even in the absence of amtB (Zhang et al., 2012, *Res. Microbiol.* 163:332-339; Yoshida et al., 2014, *J. Biosci. Bioeng.* 117:28-32). The results reported herein indicate that disruption (including, e.g., deletion) of the amtB gene in *A. vinelandii* results in a slow release of ammonium into the media. While the levels of ammonium detected in strain AZBB102 were low, these were consistently and significantly higher than what was found in the wild-type strain control (FIG. 5). A further elemental analysis of carbon, hydrogen, and nitrogen (CHN analysis) of supernatants that were collected and lyophilized did not find significant amounts of nitrogen accumulating in the supernatants, though an analysis of the cell materials found elevated nitrogen levels (3.632±0.114% nitrogen for AZBB102 versus 2.355±0.047% for wild-type, an approximately 50% increase) under the growth conditions tested here. This indicates that the low level of ammonium found from the analysis described in FIG. 5 is the most likely source of the nitrogen produced by AZBB102, and not an alternative form of nitrogen.

Potential of the AZBB103 Enhanced Biofertilizer Strain to Support the Growth of the Green Algae *C. sorokiniana*

Using co-culture on solid media (FIG. 3B) is a simple screen that provides a qualitative assessment of the ability of the strain to support algae or other organisms. In the absence of specific methods of quantitation, or if identification of the nitrogen compound responsible for supporting algal growth were unclear, cell growth of a non-diazotroph in co-culture is the clearest estimation of the potential of the strain as a biofertilizer. Co-cultures of AZBB103 and *C. sorokiniana* were grown in a simple B medium devoid of added nitrogen under a bank of fluorescent lights along with a control containing the algae and *A. vinelandii* wild-type (trans) to determine levels of algal cells that might be supported by the extracellular nitrogen being released.

Figure 6:
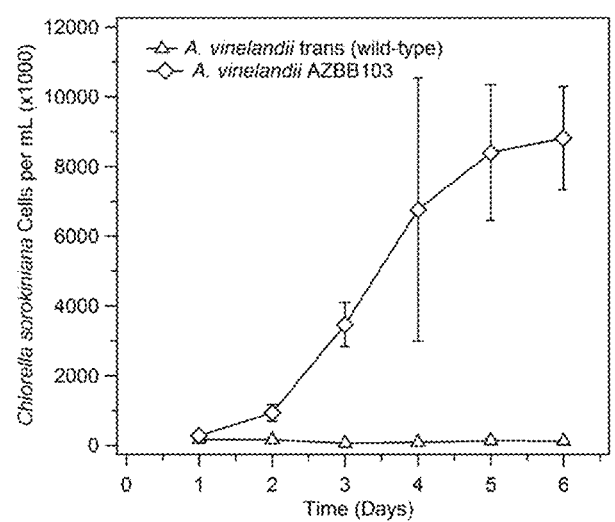
FIG. 6. Co-culture of *A. vinelandii* AZBB103 and *C. sorokiniana*. Shown above are the results obtained when *A. vinelandii* AZBB103 (containing $\Delta amtB::kan^R$ and $\Delta ureABC::strep^R$) was grown as a co-culture with *C. sorokiniana* cells over a period of six days. Cells were counted using a hemocytometer. A control containing *A. vinelandii* wild-type grown in co-culture with *C. sorokiniana* is also included for comparison. The large variance seen at day 4 for AZBB103 is potentially related to cell clumping. Following day 4, cell clumps were broken up by repeatedly passing through a pipette tip prior to counting cells. All results and statistics are calculated based on triplicate samples.

FIG. 6 shows the results of the co-culture of the ΔamtB:: $kan^R$/ΔureABC::$strep^R$ strain AZBB103 with *C. sorokiniana*. As can be seen, the levels of algae cells increased dramatically when cultured with AZBB103 versus co-culture with the wild-type *A. vinelandii*. A similar result was observed when *C. sorokiniana* was co-cultured with strain AZBB102. Improvement in the yield was greater than 50-fold after only a few days of growth. At this density, under the conditions used to co-culture the strains, the algae have likely become light limited, and were not limited by available nitrogen during the co-culture.

Reconstruction of the High Ammonium Production Phenotype

Since the ΔamtB::$kan^R$ phenotype appears to be differentiated from what has been reported for disruptions to the nifLA operon, and since initial efforts to reconstruct a similar high ammonium excreting phenotype were only partially successful (nif+ phenotype, but no increase in ammonium in the medium for strain AZBB020), a strain that excretes ammonium was constructed.

Using an approach previous described (Brewin et al., 1999, *J. Bacteriol.* 181(23):7356-7362), a plasmid similar to pBB369 (pPCRNH3-42) was constructed and used to transform strain AZBB010. Kanamycin-resistant colonies were isolated (strain AZBB148). Strain AZBB148 was confirmed to have incorporated the kanamycin resistance cassette in the proper location and direction in the genome, but did not yield a nif+ phenotype. A slightly different strain transformed with plasmid pPCRNH3-43 (strain AZBB150) also did not yield a nif+ phenotype. However, when each of these strains was transferred to liquid cultures of B medium devoid of an added nitrogen source, spontaneous mutants arose after several days that were nif+ and accumulated high levels of ammonium in the medium. These evolved strains were isolated on solid media and designated AZBB158 and AZBB163, respectively. Strain AZBB158 was grown in B medium similar to what was done for strain AZBB102 and *A. vinelandii* trans (wild-type) and was found to yield ammonium at levels approaching 10 mM after four days of growth at 22° C., differentiating strain AZBB158 from the phenotype found with ΔamtB::$kan^R$ (FIG. 5). Levels of ammonium measured following depletion of the sucrose from the media reached greater than 20 mM after more than a week of culture at 22° C. (approximately 35 mM at 30° C. for strain AZBB163).

Figure 7:
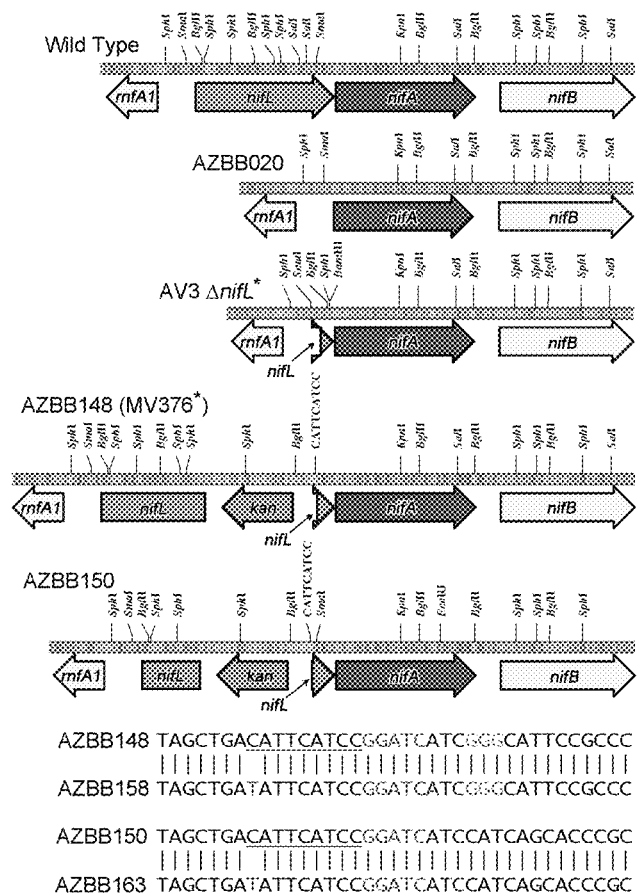
FIG. 7. Illustration of different approaches to deregulate nitrogen fixation and excrete ammonium through manipulation of the nifLA operon. Shown is an illustration of the nifLA genome region from *A. vinelandii* (wild-type) and various final constructs. The $\Delta nifLA::nifA$ construct strain AZBB020 resulted in a nitrogen-fixing (nif$^+$) phenotype, but did not increase levels of ammonium in the extracellular space, as initially anticipated. The strain AV3 $\Delta nifL$ (Ortiz-Marquez et al., 2012, *Appl. Environ. Microbiol.* 78:2345-2352) took a similar approach, but left a small segment of nifL intact, and resulted in µM levels of ammonium and a nif$^+$ phenotype (drawn as described in Ortiz-Marquez et al., 2012, *Appl. Environ. Microbiol.* 78:2345-2352). Strain AZBB148 was constructed similar to the approach to construct strains MV376 and MD367 (Bali et al., 1992, *Appl. Environ. Microbiol.* 58:1711-1718; Brewin et al., 1999, *J. Bacteriol.* 181:7356-7362), except that pPCRKAN4 was used as the source of the kanamycin cassette instead of pUC4-KIXX. Strain AZBB150 was constructed so that this same pPCRKAN4 derived kanamycin cassette would be inserted into nifL slightly further upstream while removing a larger section of the nifL gene. Both strains AZBB148 and AZBB150 were found to be nif$^-$, but became nif$^+$ following a spontaneous mutation to yield strain AZBB158 and AZBB163. The location of this mutation (underlined region) is shown in the alignments (SEQ ID NO:41; SEQ ID NO:42; SEQ ID NO:43; and SEQ ID NO:44) and is also marked on the illustration for the nifLA region of each of these strains. Sequence shown in green represents the remainder of the polished BamHI site, while sequence drawn in blue is the remnant of the EcoRV site. The remainder of the SmaI site used here and previously to construct strains MV376 and MD367 (Bali et al., 1992, *Appl. Environ. Microbiol.* 58:1711-1718; Brewin et al., 1999, *J. Bacteriol.* 181:7356-7362) is shown in orange for strains AZBB148 and AZBB158. The C to T mutation for strains AZBB158 and AZBB163 are shown in red.

The nifLA region of both strains AZBB158 and AZBB163 were amplified and sequenced and found to contain a point mutation to each residing in the segment of DNA upstream of the kanamycin promoter (FIG. 7). This mutation was in the same location of the kanamycin cassette in both of the evolved nif+ strains (AZBB158 and AZBB163), and lies in close proximity to the BamHI restriction site that is used to shuttle the kanamycin cassette between vectors. As shown in FIG. 7, the kanamycin cassette from pPCRKAN4 contains the sequence CCCAG<u>TAGCT</u> ((SEQ ID NO:1), where the underlined TAGCT is shown in FIG. 7) that is derived from Tn5. This CCCAGTAGCT sequence (SEQ ID NO:1) is the same in both the pPCRKAN4 kanamycin cassette and the pUC4-KIXX cassette (Baranay F, 1985, *Gene* 37:111-123; Yamamoto et al., 2008, *J. Bacteriol.* 190:1308-1316)). Following the CCCAGTAGCT sequence (SEQ ID NO:1), the pPCRKAN4 also contains GACATTCATCC (SEQ ID NO:2) and GGATCATC (SEQ ID NO:3). The GACATTCATCC (SEQ ID NO:2) is also derived from Tn5. The only difference between strain AZBB148 and strain MV376 (Bali et al., 1992, *Appl. Environ. Microbiol.* 58:1711-1719)) in this region is this GACATTCATCC (SEQ ID NO:2) and GGATCATC (SEQ ID NO:3) sequences in AZBB148 that is in place of CGAGAAGCTTCCC (SEQ ID NO:4) in MV376. The modification to strain AZBB148 and AZBB150 that resulted in the nif+ phenotype was GA<u>T</u>ATTCATCCGGATCATC (SEQ ID NO:5), where the C mutated to the underlined T.

Thus, this disclosure describes, in one aspect, a diazotrophic microbe genetically modified to excrete a nitrogen-containing compound such as, for example, urea and/or ammonium, in an amount greater than a comparable control diazotrophic microbe. As used herein, a comparable control diazotrophic microbe refers to a diazotrophic microbe lacking the genetic modifications that allow the modified microbe to excrete a nitrogen-containing compound such as, for example, a naturally-occurring, wild-type version of the diazotrophic microbe. In another aspect, this disclosure describes methods that involve co-culture of such a genetically-modified diazotrophic microbe with a non-diazotroph. In these methods, the genetically-modified diazotrophic microbe can act as a fertilizer, providing fixed nitrogen to the non-diazotroph and, consequently, increase the growth rate of the non-diazotroph.

In some embodiments, the genetically-modified diazotrophic microbe can be derived from *Azotobacter vinelandii*. As used herein, "derived from" of the term "or derived from" in connection with a microbe simply allows for the host cell to possess one or more genetic modifications before being modified to excrete a nitrogen-containing compound.

Efforts to convert urea into a terminal nitrogen compound resulted in μM levels of urea accumulating in the medium. The levels of urea nitrogen obtained by deleting the urease are similar to the total nitrogen produced by strain AV3 ΔnifL (Ortiz-Marquez et al., 2012, *Appl. Environ. Microbiol.* 78:2345-2352) using their initial approach to produce elevated levels of ammonium.

A complete deletion of nifL resulted in a nif⁺ phenotype but no significant accumulation of ammonium in the growth medium versus wild-type. After considerable additional effort, an ammonium-accumulating strain was isolated, first isolating the strain in the presence of a fixed nitrogen source in the media (as this strain was nif⁻), and then isolation of a spontaneous nif⁺ deletion that resulted in the production of ~10 mM ammonium after four days of culture. Disruption and/or deletion of amtB identified using the screening technique described here resulted in ammonium accumulation in the extracellular space that was capable of supporting the growth of non-diazotrophs in co-culture. The overall levels of ammonium quantified in the supernatants were significantly higher than what was found for the wild-type strain (FIG. 5). Co-culture with a non-diazotroph that can use the ammonium may deplete this nitrogen reservoir, driving additional ammonium across the membrane of the genetically-modified *A. vinelandii* by diffusion to maintain an effective amount of ammonium flux across the membrane.

The identification of the amtB disruption demonstrates how the screening approach using a nitrogen biosensor strain can yield new strains producing elevated extracellular nitrogen products regardless of whether the specific nitrogen compound produced was an initial target. This broad screening potential could have further benefits in identifying additional potential "nitrogen shuttle" compounds that might have further utility for providing nitrogen in co-culture. *A. vinelandii* also produces additional nitrogen shuttle compounds such as siderophores that are suitable for supporting the growth of algae in co-culture. In these studies, the levels of nitrogen released to the culture medium by the amtB disruption were in the low μM range, which may have been undetectable using conventional, less sensitive assays.

None of strains AZBB030, AZBB102, and AZBB103 required introducing any foreign nitrogen metabolism coding regions. Both disruptions that were shown to increase extracellular nitrogen levels by deleting/replacing ureABC (resulting in μM levels of urea accumulating in culture) and deleting or disrupting amtB (resulting in the production of sufficient ammonium to support non-diazotrophs in co-culture) could also be constructed as deletions using markerless techniques or congression approaches (Dos Santos P, 2011, *Methods Mol. Biol.* 766:81-92), resulting in true single coding region deletions that would not be transgenic, but simply gene deficient. Each of these modifications could be coupled to one another or combined with approaches that alter the nifLA operon to enhance total nitrogen output further.

The construction of stable genetic constructs that lack foreign coding regions can yield biofertilizer strains with a strong potential for use in, for example, algal culture, and potentially to be applied to additional current conventional agricultural crops as an enhanced biofertilizer.

Figure 8:
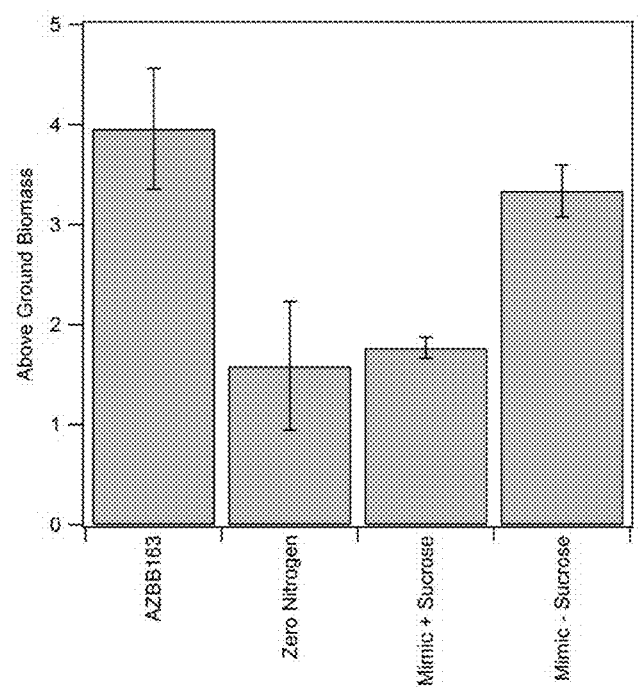
FIG. 8. Results from plant growth experiments with corn and *Azotobacter vinelandii* strain AZBB163 versus controls with no added nitrogen and a mimic containing equivalent nitrogen to that found from *Azotobacter vinelandii* strain AZBB163 with or without equivalent amounts of sugar.

In an exemplary application, corn plants that received culture and spent medium of *Azotobacter vinelandii* strain AZBB163 grown on standard growth medium showed the greatest biomass for both above and below ground mass. These results showed almost a 2.5-fold improvement in above ground mass (FIG. 8). Plants that contained a solution to mimic both the ammonium levels obtained from the *Azotobacter vinelandii* strain AZBB163 and also containing the sucrose levels that were initially used to grow this strain, did not do as well. Plants provided only a solution to mimic the ammonium levels obtained in the *Azotobacter vinelandii* strain AZBB163, but not the added sucrose showed comparable growth to that obtained with *Azotobacter vinelandii* strain AZBB163.

Two clones of *Azotobacter vinelandii* were isolated following transposon mutagenesis that resulted in improved nitrogen release when disrupting gene Avin_26490 which codes for a gene titled nifA2. This gene is a homolog to nifA of the nifLA operon which has been well characterized. This finding is somewhat unexpected, as it is counter-intuitive to what is proposed for the mechanism of action in the nifLA operon. NifL is proposed to act as a regulatory element, repressing nitrogenase gene transcription when ammonium levels in the cell are elevated. Disruption of nifL while leaving nifA expression intact results in an extreme case where nitrogenase transcription is grossly upregulated. Following the same logic, nifA2 would be expected to behave similar to nifA, and elevated levels should then increase nitrogen production, while disruption should have no effect or would be expected to lower nitrogenase expression. One of the transposon disruptions sites is well within the gene (approximately one third of the way through the gene sequence) and would be expected to eliminate expression of an intact gene product, and both deletions resulted in the production of elevated levels of ammonium (approximately 5 mM after several days of growth). Both disruptions were isolated using a screen that included a common strain of algae, indicating a broad potential application of this phenotype, similar to those described previously (Barney et al., 2015, *Appl. Environ. Microbiol.* 81:4316-4328).

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Bacteria Culture

*A. vinelandii* trans (a highly transformable version of the wild-type D J strain) was obtained from Dennis Dean (Virginia Polytechnic Institute and State University, Blacksburg, V A) and grown on standard B plates (Dos Santos P, 2011, *Methods Mol. Biol.* 766:81-92) unless otherwise specified. *Escherichia coli* WM3064 was used for conjugation (Brutinel E D, Gralnick J A, 2012, *Mol. Microbiol.* 86:273-283; Lenneman et al., 2013, *Appl. Environ. Microbiol.* 79:7055-7062) and grown on Lysogeny Broth (LB) or on BYE (B plates containing 5 g/L of yeast extract).

Algal Culture and Cell Counts

Cultures of *Chlorella sorokiniana* UTEX 1602 were obtained from the UTEX culture collection of algae (Austin, Tex.) and have been maintained for several years by sub-culturing on solid media (Torrecilla et al., 2014, *FEMS Microbiol. Lett.* 351:70-77). Algae strains were cultured in a freshwater medium as described previously (Lenneman at el., 2014, *FEMS Microbiol. Lett.* 354:102-110). Algal cells in solution were measured using a hemocytometer following the directions of the manufacturer (Hausser Scientific, Horsham, Pa.).

Initial Genetic Constructs of *Azotobacter vinelandii*

*Azotobacter vinelandii* strains AZBB030 and AZBB035 used as target strains, and AZBB063 used as a biosensor strain, were constructed as detailed in Table 1 by transforming *A. vinelandii* trans with various plasmids listed in Table 2. Primers used to clone genes or genome segments are listed in Table 3. A graphical representation of the three strains as compared to the wild-type *A. vinelandii* trans strain is shown on the top of FIG. 2. Following the transposon experiments described below, *A. vinelandii* strains AZBB102, AZBB103, AZBB148 and AZBB150 were constructed by using a similar approach to confirm the phenotype found during the transposon experiments. Methods for the manipulation of *A. vinelandii* have been described previously (Dos Santos P C, 2011, *Methods Mol. Biol.* 766:81-92; Barney et al., 2009, *J. Biol. Inorg. Chem.* 14:1015-1022; Sarma et al., 2008, *Biochemistry* 47:13004-13015).

TABLE 1

Mutant strains constructed and/or used in this study.

| Strain | Plasmid utilized | Genetic features | Parent Strain |
| --- | --- | --- | --- |
| *A. vinelandii* trans (DJ) | None | Wild-type | (1) |
| AZBB010 | pPCRNH3-15 | ΔnifLA::strep$^R$ | *A. vinelandii* trans (DJ) |
| AZBB020 | pPCRNH3-14 | ΔnifLA::nifA | AZBB010 |
| AZBB023 | pPCRSCRK31 | ΔscrX::lacZ-kan$^R$ | *A. vinelandii* trans (DJ) |
| AZBB030 | pPCRURE3 | ΔureABC::strep$^R$ | *A. vinelandii* trans (DJ) |
| AZBB035 | pPCRURE3 | ΔureABC::strep$^R$ and ΔnifLA::nifA | AZBB020 |
| AZBB063 | pPCRNH3-21 | ΔnifLA::tet$^R$ and ΔscrX::lacZ-kan$^R$ | AZBB023 |
| AZBB085 | pTNMme1 | amtB:kan$^R$-transposon and ΔureABC::strep$^R$ and ΔnifLA::nifA | AZBB035 |
| AZBB086 | pTNMme1 | amtB:kan$^R$-transposon and ΔureABC::strep$^R$ and ΔnifLA::nifA | AZBB035 |
| AZBB088 | pTNMme1 | amtB:kan$^R$-transposon and ΔureABC::strep$^R$ | AZBB030 |
| AZBB091 | pTNMme1 | amtB:kan$^R$-transposon and ΔureABC::strep$^R$ | AZBB030 |
| AZBB093 | pTNMme1 | amtB:kan$^R$-transposon and ΔureABC::strep$^R$ and ΔnifLA::nifA | AZBB035 |
| AZBB094 | pTNMme1 | amtB:kan$^R$-transposon and ΔureABC::strep$^R$ and ΔnifLA::nifA | AZBB035 |
| AZBB102 | pPCRAMTBK3 | ΔamtB.:kan$^R$ | *A. vinelandii* trans (DJ) |
| AZBB103 | pPCRAMTBK3 | ΔamtB::kan$^R$ and ΔureABC::strep$^R$ | AZBB030 |
| AZBB148 | pPCRNH3-42 | nifL::kan$^R$ similar to MV376 (2) | AZBB010 |
| AZBB150 | pPCRNH3-43 | nifL::kan$^R$ incorporated slightly upstream of SmaI site | AZBB010 |
| AZBB158 | none | Spontaneous mutation of AZBB148 resulting in nif$^+$ phenotype | AZBB148 |
| AZBB163 | none | Spontaneous mutation of AZBB150 resulting in nif$^+$ phenotype | AZBB150 |

(1) Setubal et al., 2009, J. Bacteriol. 191: 4534-4545

(2) Brewin et al., 1999, J. Bacteriol. 181: 7356-7362

TABLE 2

Plasmids and relevant derivatives used for the construction of *Azotobacter vinelandii* manipulated strains

| Plasmid[a] | Relevant Genes Cloned or Plasmid Manipulation | Parent Vector | Reference and/or Source |
|---|---|---|---|
| pTNMme1 | Plasmid containing Mariner transposon and transposase | pEB001 | (3) |
| pBB052 | pUC19 with Kan resistance from pUC4K in place of Amp. | pUC19 | (4) |
| pBB053 | Removed NdeI site from pUC19 by silent mutation | pUC19 | (5) |
| pBB073 | Moved Spectinomycin/Streptomycin resistance cassette from pHP45Ω into EcoRI site of pBB052 | pBB052 | (6) |
| pBBTET3 | pUC19 with Tet resistance in place of Amp | pUC19 | (5) |
| pPCRKAN4 | Cloned Kan cassette from pBBR1MCS-2 into pBBTET3 | pBBTET3 | (5) |
| pLACZF12 | Cloned lacZ gene from *E. coli* into pBBTET3 and removed various restriction sites by silent mutation with site-specific mutagenesis | pBBTET3 | This Study |
| pPCRSCRK2 | Cloned scrX gene and flanking regions from *A. vinelandii* into pBB053 | pBB053 | This Study |
| pPCRSCRK5 | Removed restriction sites from pPCRSCRK2 by blunt fill-in. Performed PCR to remove scrX gene from plasmid | pBB053 | This Study |
| pPCRSCRK7 | Performed additional blunt fill-in and site-specific mutagenesis to remove additional restriction sites | pBB053 | This Study |
| pPCRSCRK28 | Moved Kan cassette from pPCRKAN4 into pPCRSCRK7, then removed restriction sites by site-specific mutagenesis with silent mutations | pBB053 | This Study |
| pPCRSCRK31[b] | Moved lacZ gene from pLACZF12 into pPCRSCRK28 | pBB053 | This Study |
| pPCRNH3-10 | Cloned nifA gene from *A. vinelandii* into pBB114 | pBB114 | This Study |
| pPCRNH3-11 | Cloned nifLA genes and flanking regions from *A. vinelandii* into pBB053 | pBB053 | This Study |
| pPCRNH3-12 | Removed restriction site from pPCRNH3-11 by blunt fill-in | pBB053 | This Study |
| pPCRNH3-13 | Performed PCR to remove nifLA genes from pPCRNH3-12 and add XbaI and BamHI sites | pBB053 | This Study |
| pPCRNH3-14[b] | Moved nifL gene from pPCRNH3-10 into pPCRNH3-13 | pBB053 | This Study |
| pPCRNH3-15[b] | Moved Strep cassette from pBB073 into pPCRNH3-13 | pBB053 | This Study |
| pPCRNH3-21[b] | Moved Tet cassette pBBTET3 into pPCRNH3-13 | pBB053 | This Study |
| pPCRNH3-42 | Removed segment of nifL gene from pPCRNH3-11 and inserted Kan cassette from pPCRKAN4 similar to approach taken to construct pBB369 (7) | pBB053 | This Study and (7) |
| pPCRNH3-43 | Removed larger segment of nifL gene from pPCRNH3-11 than was done in pPCRNH3-42 and inserted Kan cassette from pPCRKAN4 slightly further upstream of nifA as shown in FIG. 7 | pBB053 | This Study |
| pPCRURE1 | Cloned ureABC genes and flanking regions from *A. vinelandii* into pUC19 | pUC19 | This Study |
| pPCRURE2 | Performed PCR to remove ureABC genes from pPCRURE1 | pUC19 | This Study |
| pPCRURE3[b] | Moved Strep cassette pBB073 into pPCRURE2 | pUC19 | This Study |
| pPCRAMTBK1 | Cloned gene amtB and flanking regions from *A. vinelandii* into pBB053 | pBB053 | This Study |
| pPCRAMTBK2 | Performed PCR to remove gene amtB from pPCRAMTBK1 | pBB053 | This Study |
| pPCRAMTBK3[b] | Moved Kan cassette from pPCRKAN4 into pPCRAMTBK2 | pBB053 | This Study |

[a]Sequences of all plasmids in this study are available upon request
[b]Plasmids shown in bold are completed vectors used to transform *A. vinelandii*
(3) Brutinel ED and Gralnick JA, 2012,/146/. Microbiol. 86: 273-283
(4) Taylor LA and Rose RE, 1988, Nucleic Acids Res. 16: 358
(5) Lenneman et al., 2013, Appl. Environ. Microbiol. 79: 7055-7062
(6) Prentki P and Krisch HM, 1984, Gene 29: 303-313
(7) Brewin et al., 1999, J. Bacteriol. 181: 7356-7362

TABLE 3

Primers used in this study

| Primer Designation | Primer Sequence[a] | Purpose |
|---|---|---|
| BBP919 | 5'-GACTAGAA TTCGTGCAGA AACATCTCTA CCCGGAAG-3' (SEQ ID NO: 6) | ureABC genes and flanking region cloning |
| BBP920 | 5'-GACTAAAG CTTGGAACAG AAGACGATGA GGATGC-3' (SEQ ID NO: 7) | ureABC genes and flanking region cloning |
| BBP938 | 5'-GACTAGGA TCCGTGAAGA TCAGCAGCTT GTCTTTCTC-3' (SEQ ID NO: 8) | ureABC genes deletion |
| BBP939 | 5'-GACTAGGA TCCAAGAAGG ACCTGATCCA CAACG-3' (SEQ ID NO: 9) | ureABC genes deletion |

TABLE 3-continued

Primers used in this study

| Primer Designation | Primer Sequence[a] | Purpose |
|---|---|---|
| BBP1147 | 5'-GAGCAAGC TTCATGGTCA GGTCGTGGCC TTC-3' (SEQ ID NO: 10) | nifLA genes and flanking region cloning |
| BBP1148 | 5'-GACAGGAT CCGGTCAGCA CTTCGGACAC CAC-3' (SEQ ID NO: 11) | nifLA genes and flanking region cloning |
| BBP1209 | 5'-GACATCTA GACTCTCATA TGGTGCCTCG TCTATCCAAG AAAACC-3' (SEQ ID NO: 12) | nifLA genes deletion |
| BBP1210 | 5'-GACATCTA GAGGATCCGA CCCTCCGGCA ATGGATG-3' (SEQ ID NO: 13) | nifLA genes deletion |
| BBP1149 | 5'-GACAGGAT CCATATGAAT GCAACCATCC CTCAGCGCT C-3' (SEQ ID NO: 14) | nifA gene cloning |
| BBP1150 | 5'-GACATCTA GACTAGATCT TGCGCATGTG GATGTTGAG-3' (SEQ ID NO: 15) | nifA gene cloning |
| BBP2099 | 5'-NNNGATAT CGGGCATTCC GCCCGACCTG GTGCTG-3' (SEQ ID NO: 16) | MIL gene segment deletion 1 |
| BBP2100 | 5'-NNNGATAT CGACGACGAT GCCCTGGGCC AGCAACTG-3' (SEQ ID NO: 17) | MIL gene segment deletion 1 |
| BBP2101 | 5'-NNNGATAT CCCGGAGAAG GCGCTGCCCT G-3' (SEQ ID NO: 18) | MIL gene segment deletion 2 |
| BBP2102 | 5'-NNNGATAT CCATCAGCAC CGCGTGGAG AAC-3' (SEQ ID NO: 19) | MIL gene segment deletion 2 |
| BBP1674 | 5'-NNNTCTAG AGGAAGCTAT CCGACGAGGA CAGCCGAG-3' (SEQ ID NO: 20) | scrX gene and flanking region cloning |
| BBP1675 | 5'-NNNGAATT CCTGAGCGCA GAATTTAGAT ATTGATACTC ATAGTC-3' (SEQ ID NO: 21) | scrX gene and flanking region cloning |
| BBP1710 | 5'-NNNATGCA TATGGACTTC CTATTGTTGA CATTATTGGT GG-3' (SEQ ID NO: 22) | scrX gene deletion |
| BBP1711 | 5'-NNNATGCA TGACAGAATT CAGATCTCAC GCCATAAGCT GTTAGCATTT TTCTTG-3' (SEQ ID NO: 23) | scrX gene deletion |
| BBP1669 | 5'-NNNTCTAG AGGATCCCAT ATGCATACCA TGATTACGGA TTCACTGGCC GTCG-3' (SEQ ID NO: 24) | lacZ gene cloning |
| BBP1671 | 5'-NNNAAGCT TGGATCCTAT TTTTGACAC CAGACCAACT GGTAATGGTA G-3' (SEQ ID NO: 25) | lacZ gene cloning |
| BBP1967 | 5'-NNNAAGCT TCGAAGACAT GGCACTCCGA GGCGTTGGCC AGAC-3' (SEQ ID NO: 26) | amtB gene and flanking region cloning |
| BBP1968 | 5'-NNNTCTAG AGATAGATTC CCTGCCAGGT CCCCAG-3' (SEQ ID NO: 27) | amtB gene and flanking region cloning |
| BBP1968 | 5'-NNNAGATC TGGTTACAAC CTCTGAGTGT CGGGAG-3' (SEQ ID NO: 28) | amtB gene deletion |
| BBP1970 | 5'-NNNAGATC TCAGCGTCAT TGATTATTCT CCTGGGGCG-3' (SEQ ID NO: 29) | amtB gene deletion |
| BBP982 | 5'-GAAGGGCA GCAGCAGGTA GAGG-3' (SEQ ID NO: 30) | ureABC gene deletion confirmation |
| BBP983 | 5'-CAGCAGTT CGCGAAGACT GTCGAAG-3' (SEQ ID NO: 31) | ureABC gene deletion confirmation |
| BBP1836 | 5'-CTCAACGT TCGCCAGGTA TATGCCGAAC TC-3' (SEQ ID NO: 32) | scrX gene deletion confirmation |
| BBP1837 | 5'-CACATAGG ATGAAACGTC ACCGAGCTTG TTCG-3' (SEQ ID NO: 33) | scrX gene deletion confirmation |

TABLE 3-continued

Primers used in this study

| Primer Designation | Primer Sequence[a] | Purpose |
|---|---|---|
| BBP950 | 5'-GAGCACAC CCATCACGGT CAGAG-3' (SEQ ID NO: 34) | nifLA gene deletion confirmation |
| BBP1322 | 5'-GATCTCCA TCGACTCGAT CTTGTCCAGG GTGAAC-3' (SEQ ID NO: 35) | nifLA gene deletion confirmation |
| BBP2006 | 5'-CACGTGCC AGGAATTCCT CCATG-3' (SEQ ID NO: 36) | amtB gene deletion confirmation |
| BBP2007 | 5'-CTGTGGAC GATGGCCAGG GACATGGATC-3' (SEQ ID NO: 37) | amtB gene deletion confirmation |

[a]Specific restriction enzyme sites added to primers are underlined for clarity Urea Quantitation To measure extracellular urea concentrations from cultures of A. vinelandii, 1 mL samples were first spun at maximum speed on a microcentrifuge for 1 minute (~21,000×g), then the supernatant was removed and stored at −80° C. or used immediately. Urea was quantified as previously described (Mather A and Roland D, 1969, Clin. Chem. 15:393-396) with slight alterations. Reagent was prepared fresh immediately before use by dissolving 10 mg of $FeCl_3.6H_2O$ in 50 mLs of acid solution (8% $H_2SO_4$ and 1% $H_3PO_4$). Next, 75 mg of diacetyl monoxime was dissolved in 5 mL of $H_2O$ and combined with the acid solution. Then 5 mg of thiosemicarbazide was dissolved in 5 mL of $H_2O$ and combined with the acid solution. A standard curve was prepared with a maximum concentration of 1 mM Urea. To run the assay, 300 μL of sample or standard was combined with 1 mL of the reagent and mixed thoroughly in a 1.5 mL microcentrifuge tube (polypropylene). Samples were incubated for 20 minutes at 90° C., then cooled on ice and allowed to sit for 20 minutes before measuring on a UV/Visible spectrophotometer at 520 nm.

Ammonium Quantitation

Ammonium was quantified by several different methods that have been described previously (Bali et al., 1992, Appl. Environ. Microbiol. 58:1711-1718; Ortiz-Marquez et al., 2012, Appl. Environ. Microbiol. 78:2345-2352; Barney et al., 2004, J. Biol. Chem. 279:53621-53624; Kanda J, 1995, Water Res. 29:2746-2750) using either fluorescent or colorimetric approaches. For low levels of ammonium obtained from specific culture supernatants, a derivation of the phthalaldehyde method described previously (Barney et al., 2005, Biochemistry 44:8030-8037; Corbin J L, 1984, Appl. Environ. Microbiol. 47:1027-1030) was used. In these assays, 500 μL of assay reagent (270 mg phthalic dicarboxaldehyde dissolved in 5 mL of ethanol, then added to 100 mL of 0.2 M phosphate buffer pH 7.3 and 50 μL of β-mercaptoethanol) was combined with 500 μL of culture supernatant and allowed to react at room temperature for 30 minutes. Samples were analyzed on a Varian Cary Eclipse Fluorescence Spectrophotometer using an excitation wavelength of 410 nm and emission wavelength of 472 nm.

Elemental Analysis of Cells and Supernatants

Cells were collected by centrifugation at ~12,000×g and frozen. Supernatants were separated from the cells for analysis of remaining solids. Samples were lyophilized and thoroughly mixed using a spatula to assure a homogeneous mixture. Samples were analyzed for percent carbon, hydrogen and nitrogen at the Stable Isotope Lab in the Geology Department at the University of Minnesota.

Random Transposon Mutagenesis

Azotobacter vinelandii strains AZBB030 and AZBB035 were transformed by a transposon insertion methodology using Escherichia coli WM3064 and the mariner transposon from plasmid pEB001 (Brutinel E D and Gralnick J A, 2012, Mol. Microbiol. 86:273-283; Bouhenni et al., 2005, Appl. Environ. Microbiol. 71:4935-4937). Briefly, approximately 50 μL of A. vinelandii cells were scraped from a fresh agar plate of cells with a sterile loop and resuspended in 500 μL of sterile phosphate buffer. Separately, approximately 50 μL of E. coli WM3064 cells containing the pEB001 plasmid were resuspended in 1 mL of sterile LB broth. Next, 100 μL of the suspended A. vinelandii cells and 20 μL of the suspended E. coli WM3064 cells were combined and mixed with a pipettor, then spotted onto BYE plates supplemented with 100 μM of 2,6-diaminopimelic acid (DAP, 50 μL of a 10 mg/mL stock). These cells were incubated overnight at 30° C., then transferred with a sterile loop to 100 mL of B medium and grown overnight at 30° C. in a shaker table at 180 rpm. Following growth in the B medium, 1 mL of cells were removed and pelleted in a microfuge at 12,000×g, then all but 100 μL of supernatant was removed. The cells were resuspended in the 100 μL of remaining media, and plated onto B plates supplemented with kanamycin (3 μg/mL) and 5-bromo-4-chloro-3-indolyl-3-D-galactopyranoside (X-Gal, 80 μg/mL), and pretreated with a lawn of A. vinelandii strain AZBB063. Plates were then incubated at 30° C. for several days until colonies formed. Colonies were selected that revealed the blue phenotype, indicating that the integrated transposon had altered the A. vinelandii AZBB030 or AZBB035 target strains so they could support the growth of the nif very slow phenotype of the A. vinelandii AZBB063 biosensor strain. Colonies that turned blue were transferred to a B plate containing streptomycin to confirm and isolate only the transposon modified strain, then again checked for the proper blue phenotype by streaking clean isolates on an IPTG and kanamycin supplemented plate with a lawn of A. vinelandii AZBB063. False-positive colonies were further tested by streaking onto B plates containing streptomycin and X-Gal.

Transposon Insertion Analysis

Strains exhibiting the desired phenotype were first purified by streaking individual colonies several times on a B plate supplemented with streptomycin (0.5 μg/mL). Cells were then scraped from a clean plate (approximately 100 μL of cells) and genomic DNA was isolated using the ZR Fungal/Bacterial DNA Miniprep kit (Zymo Research, Irvine, Calif.). Genomic DNA was digested with PstI, then purified using the DNA Clean and Concentrator-25 kit (Zymo research) and ligated using T4 DNA Ligase (New England Biolabs, Ipswich, Mass.). PCR was then run on the ligated DNA using primer BBP1241 (5'-GACCGCTA TCA-GGACA TAGCGTTG-3'), which aligns near the end of the kan gene used as the selectable marker indicating transposon insertion. This approach relies on the potential of two similar DNA fragments containing the insert and sequence downstream the point of insertion to ligate and orient directionally toward one another. While this is a rare event, PCR can then be utilized to amplify these segments for sequencing. The PCR reactions were analyzed by gel electrophoresis to confirm amplification, then cleaned using the DNA clean and Concentrator-25 kit, and sent for Sanger sequencing with the same primer BBP1241. All sequencing products for positive phenotypes identified a segment matching between 200 and 700 bp of genomic sequence from *A. vinelandii* DJ (Setubal et al., 2009, *J. Bacteriol.* 191:4534-4545).

Co-Culture of *Azotobacter vinelandii* and *Chlorella sorokiniana*

A minimal amount of cells from strains of *A. vinelandii* and *C. sorokiniana* were spotted onto B plates substituting plant cell culture tested agar (Sigma-Aldrich, St. Louis, Mo.) for bacto-agar and grown on a custom light table for several days to make a qualitative assessment of the potential of various strains to support the growth of the algae. Equivalent starting quantities of cells were spotted to the plates. For liquid culture experiments, equivalent quantities of cells were inoculated into 60 mLs of B medium in a 125 mL Erlenmeyer flask, and grown under a bank of fluorescent lights with 14:10 light:dark cycles, while monitoring numbers of cells/mL daily. Light intensity for both experiments was approximately 200 µmols $min^{-1}$ $m^2$. Liquid cultures were mixed on a shaker table with constant shaking at 160 rpm.

Example 2

Greenhouse Plant Growth Studies

Corn seeds were planted in 8-inch azalea pots filled with a sterilized sandy-loam soil. Samples included 1) plants with no added nitrogen, 2) plants with *Azotobacter vinelandii* strain AZBB163 and spent medium grown on a standard growth medium containing sucrose, 3) plants with a similar amount of ammonium and sucrose to what was added with the *Azotobacter vinelandii* strain AZBB163 (similar quantities of ammonium to that found in part 2), or 4) plants with a similar amount of ammonia to what was added with the *Azotobacter vinelandii* AZBB163 (similar quantities of ammonium to that found in part 2), but containing no added sucrose. Plants were grown for 8 days prior to application of any nitrogen. Nitrogen was added incrementally to provide 15 total applications over a 36-day period prior to harvest.

Disruption to *Azotobacter vinelandii* Gene Avin_26490 Resulting in Increased Nitrogen Production Random mutations were induced in *Azotobacter vinelandii* through transposon mutagenesis with a nitrogen biosensor, revealing an additional gene that resulted in increased nitrogen release, using previously described methods. (Barney et al., 2015, *Appl. Environ. Microbiol.* 81:4316-4328). Two independent colonies were found with disruptions upstream and one third of the way into the gene Avin_26490, which codes for nifA2. Both genes showed a positive growth phenotype with *Chlorella sorokiniana* when utilized as a screen for extracellular nitrogen production.

Results are shown in FIG. 8.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of increasing growth of a non-diazotroph, the method comprising:
    co-culturing the non-diazotroph; and
    an *Azotobacter* spp. genetically modified to excrete a nitrogen-containing compound in an amount effective to support the growth of a non-diazotroph in co-culture, the genetic modification comprising:
    a deletion or disruption of at least a portion of ureABC;
    a deletion or disruption of at least a portion of amtB; or
    a deletion or disruption of at least a portion of nifA2;
    wherein the *Azotobacter* spp. is provided in an amount effective to increase the growth of the non-diazotroph compared to growth of the non-diazotroph in the absence of the diazotrophic microbe.

2. The method of claim 1 wherein increasing the growth of the non-diazotroph comprises increasing the growth rate of the non-diazotroph.

3. The method of claim 1 wherein increasing the growth of the non-diazotroph comprises increasing the cell density of the non-diazotroph.

4. The method of claim 1 wherein increasing the growth of the non-diazotroph comprises increasing the crop yield of the non-diazotroph.

* * * * *

SEQUENCE LISTING

<160> NUMBER OF SEQ ID NOS: 44

<210> SEQ ID NO 1
<211> LENGTH: 10
<212> TYPE: DNA
<213> ORGANISM: artificial
<220> FEATURE:
<223> OTHER INFORMATION: primer

<400> SEQUENCE: 1
cccagtagct                                                                      10

<210> SEQ ID NO 2
<211> LENGTH: 11
<212> TYPE: DNA
<213> ORGANISM: artificial
<220> FEATURE:
<223> OTHER INFORMATION: primer

<400> SEQUENCE: 2
gacattcatc c                                                                    11

<210> SEQ ID NO 3
<211> LENGTH: 8
<212> TYPE: DNA
<213> ORGANISM: artificial
<220> FEATURE:
<223> OTHER INFORMATION: primer

<400> SEQUENCE: 3 ggatcatc                                                                         8

<210> SEQ ID NO 4
<211> LENGTH: 13
<212> TYPE: DNA
<213> ORGANISM: artificial
<220> FEATURE:
<223> OTHER INFORMATION: primer

<400> SEQUENCE: 4
cgagaagctt ccc                                                                  13

<210> SEQ ID NO 5
<211> LENGTH: 19
<212> TYPE: DNA
<213> ORGANISM: artificial
<220> FEATURE:
<223> OTHER INFORMATION: primer

<400> SEQUENCE: 5
gatattcatc cggatcatc                                                            19

<210> SEQ ID NO 6
<211> LENGTH: 36
<212> TYPE: DNA
<213> ORGANISM: artificial
<220> FEATURE:
<223> OTHER INFORMATION: primer

<400> SEQUENCE: 6
gactagaatt cgtgcagaaa catctctacc cggaag                                         36

<210> SEQ ID NO 7
<211> LENGTH: 34
<212> TYPE: DNA
<213> ORGANISM: artificial
<220> FEATURE:
<223> OTHER INFORMATION: primer

<400> SEQUENCE: 7
gactaaagct tggaacagaa gacgatgagg atgc                                           34

<210> SEQ ID NO 8
<211> LENGTH: 37
<212> TYPE: DNA
<213> ORGANISM: artificial

```
<220> FEATURE:
<223> OTHER INFORMATION: primer

<400> SEQUENCE: 8
gactaggatc cgtgaagatc agcagcttgt ctttctc                              37

<210> SEQ ID NO 9
<211> LENGTH: 33
<212> TYPE: DNA
<213> ORGANISM: artificial
<220> FEATURE:
<223> OTHER INFORMATION: primer

<400> SEQUENCE: 9
gactaggatc caagaaggac ctgatccaca acg                                  33

<210> SEQ ID NO 10
<211> LENGTH: 31
<212> TYPE: DNA
<213> ORGANISM: artificial
<220> FEATURE:
<223> OTHER INFORMATION: primer

<400> SEQUENCE: 10
gagcaagctt catggtcagg tcgtggcctt c                                    31

<210> SEQ ID NO 11
<211> LENGTH: 31
<212> TYPE: DNA
<213> ORGANISM: artificial
<220> FEATURE:
<223> OTHER INFORMATION: primer

<400> SEQUENCE: 11
gacaggatcc ggtcagcact tcggacacca c                                    31

<210> SEQ ID NO 12
<211> LENGTH: 44
<212> TYPE: DNA
<213> ORGANISM: artificial
<220> FEATURE:
<223> OTHER INFORMATION: primer

<400> SEQUENCE: 12
gacatctaga ctctcatatg gtgcctcgtc tatccaagaa aacc                      44

<210> SEQ ID NO 13
<211> LENGTH: 35
<212> TYPE: DNA
<213> ORGANISM: artificial
<220> FEATURE:
<223> OTHER INFORMATION: primer

<400> SEQUENCE: 13
gacatctaga ggatccgacc ctccggcaat ggatg                                35

<210> SEQ ID NO 14
<211> LENGTH: 38
<212> TYPE: DNA
<213> ORGANISM: artificial
<220> FEATURE:
<223> OTHER INFORMATION: primer

<400> SEQUENCE: 14
gacaggatcc atatgaatgc aaccatccct cagcgctc                             38
```

-continued

<210> SEQ ID NO 15
<211> LENGTH: 37
<212> TYPE: DNA
<213> ORGANISM: artificial
<220> FEATURE:
<223> OTHER INFORMATION: primer

<400> SEQUENCE: 15
gacatctaga ctagatcttg cgcatgtgga tgttgag                             37

<210> SEQ ID NO 16
<211> LENGTH: 34
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 16
nnngatatcg ggcattccgc ccgacctggt gctg                                34

<210> SEQ ID NO 17
<211> LENGTH: 36
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 17
nnngatatcg acgacgatgc cctgggccag caactg                              36

<210> SEQ ID NO 18
<211> LENGTH: 29
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 18
nnngatatcc cggagaaggc gctgccctg                                      29

<210> SEQ ID NO 19
<211> LENGTH: 31
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 19
nnngatatcc atcagcaccc gcgtggagaa c                                   31

<210> SEQ ID NO 20
<211> LENGTH: 36

-continued

```
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 20
nnntctagag gaagctatcc gacgaggaca gccgag                              36

<210> SEQ ID NO 21
<211> LENGTH: 44
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 21
nnngaattcc tgagcgcaga atttagatat tgatactcat agtc                    44

<210> SEQ ID NO 22
<211> LENGTH: 40
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 22
nnnatgcata tggacttcct attgttgaca ttattggtgg                         40

<210> SEQ ID NO 23
<211> LENGTH: 54
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 23
nnnatgcatg acagaattca gatctcacgc cataagctgt tagcattttt cttg         54

<210> SEQ ID NO 24
<211> LENGTH: 52
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 24
nnntctagag gatcccatat gcataccatg attacggatt cactggccgt cg           52

<210> SEQ ID NO 25
```

```
<211> LENGTH: 48
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 25
nnnaagcttg gatcctattt ttgacaccag accaactggt aatggtag           48

<210> SEQ ID NO 26
<211> LENGTH: 42
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 26
nnnaagcttc gaagacatgg cactccgagg cgttggccag ac                 42

<210> SEQ ID NO 27
<211> LENGTH: 34
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 27
nnntctagag atagattccc tgccaggtcc ccag                          34

<210> SEQ ID NO 28
<211> LENGTH: 34
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 28
nnnagatctg gttacaacct ctgagtgtcg ggag                          34

<210> SEQ ID NO 29
<211> LENGTH: 37
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t

<400> SEQUENCE: 29
nnnagatctc agcgtcattg attattctcc tggggcg                       37
```

<210> SEQ ID NO 30
<211> LENGTH: 22
<212> TYPE: DNA
<213> ORGANISM: artificial
<220> FEATURE:
<223> OTHER INFORMATION: primer

<400> SEQUENCE: 30
gaagggcagc agcaggtaga gg                                             22

<210> SEQ ID NO 31
<211> LENGTH: 25
<212> TYPE: DNA
<213> ORGANISM: artificial
<220> FEATURE:
<223> OTHER INFORMATION: primer

<400> SEQUENCE: 31
cagcagttcg cgaagactgt cgaag                                          25

<210> SEQ ID NO 32
<211> LENGTH: 30
<212> TYPE: DNA
<213> ORGANISM: artificial
<220> FEATURE:
<223> OTHER INFORMATION: primer

<400> SEQUENCE: 32
ctcaacgttc gccaggtata tgccgaactc                                     30

<210> SEQ ID NO 33
<211> LENGTH: 32
<212> TYPE: DNA
<213> ORGANISM: artificial
<220> FEATURE:
<223> OTHER INFORMATION: primer

<400> SEQUENCE: 33
cacataggat gaaacgtcac cgagcttgtt cg                                  32

<210> SEQ ID NO 34
<211> LENGTH: 23
<212> TYPE: DNA
<213> ORGANISM: artificial
<220> FEATURE:
<223> OTHER INFORMATION: primer

<400> SEQUENCE: 34
gagcacaccc atcacggtca gag                                            23

<210> SEQ ID NO 35
<211> LENGTH: 34
<212> TYPE: DNA
<213> ORGANISM: artificial
<220> FEATURE:
<223> OTHER INFORMATION: primer

<400> SEQUENCE: 35
gatctccatc gactcgatct tgtccagggt gaac                                34

<210> SEQ ID NO 36
<211> LENGTH: 23
<212> TYPE: DNA
<213> ORGANISM: artificial
<220> FEATURE:
<223> OTHER INFORMATION: primer

<400> SEQUENCE: 36
cacgtgccag gaattcctcc atg                                    23

<210> SEQ ID NO 37
<211> LENGTH: 28
<212> TYPE: DNA
<213> ORGANISM: artificial
<220> FEATURE:
<223> OTHER INFORMATION: primer

<400> SEQUENCE: 37
ctgtggacga tggccaggga catggatc                               28

<210> SEQ ID NO 38
<211> LENGTH: 19
<212> TYPE: DNA
<213> ORGANISM: Azotobacter vinelandii

<400> SEQUENCE: 38
agaataatca atgacgctg                                         19

<210> SEQ ID NO 39
<211> LENGTH: 20
<212> TYPE: DNA
<213> ORGANISM: Azotobacter vinelandii

<400> SEQUENCE: 39
tgttcggtta tagcttggcc                                        20

<210> SEQ ID NO 40
<211> LENGTH: 22
<212> TYPE: DNA
<213> ORGANISM: Azotobacter vinelandii

<400> SEQUENCE: 40
ttcaccgtga tctacaccgg cg                                     22

<210> SEQ ID NO 41
<211> LENGTH: 36
<212> TYPE: DNA
<213> ORGANISM: Azotobacter vinelandii

<400> SEQUENCE: 41
agctgacatt catccggatc atcgggcatt ccgccc                      36

<210> SEQ ID NO 42
<211> LENGTH: 36
<212> TYPE: DNA
<213> ORGANISM: Azotobacter vinelandii

<400> SEQUENCE: 42
agctgatatt catccggatc atcgggcatt ccgccc                      36

<210> SEQ ID NO 43
<211> LENGTH: 37
<212> TYPE: DNA
<213> ORGANISM: Azotobacter vinelandii

<400> SEQUENCE: 43
tagctgacat tcatccggat catccatcag cacccgc                     37

<210> SEQ ID NO 44
<211> LENGTH: 37

```
<212> TYPE: DNA
<213> ORGANISM: Azotobacter vinelandii

<400> SEQUENCE: 44
tagctgatat tcatccggat catccatcag cacccgc                              37
```